United States Patent
Botos et al.

(10) Patent No.: US 7,420,298 B2
(45) Date of Patent: *Sep. 2, 2008

(54) WATER COOLED HIGH PRECISION Z-THETA STAGE

(75) Inventors: Stephen J. Botos, Pittsburgh, PA (US); Brian P. O'Connor, Allison Park, PA (US)

(73) Assignee: Aerotech, Inc., Pittsburgh, PA (US)

( * ) Notice: Subject to any disclaimer, the term of this patent is extended or adjusted under 35 U.S.C. 154(b) by 541 days.

This patent is subject to a terminal disclaimer.

(21) Appl. No.: 11/169,514

(22) Filed: Jun. 29, 2005

(65) Prior Publication Data
US 2006/0017330 A1   Jan. 26, 2006

Related U.S. Application Data

(63) Continuation-in-part of application No. 10/830,979, filed on Apr. 23, 2004, now Pat. No. 7,105,956.

(51) Int. Cl.
*B23K 26/00* (2006.01)
(52) U.S. Cl. .................... 310/12; 219/121.67
(58) Field of Classification Search .......... 310/12, 310/54; 219/121.67, 121.72, 71, 82, 83; 29/759; 409/165–168, 235
See application file for complete search history.

(56) References Cited

U.S. PATENT DOCUMENTS

| | | | | | |
|---|---|---|---|---|---|
| 4,896,869 | A | * | 1/1990 | Takekoshi | 269/60 |
| 5,939,808 | A | * | 8/1999 | Adames | 310/89 |
| 6,356,219 | B1 | | 3/2002 | Weibel, IV et al. | |
| 6,511,504 | B1 | | 1/2003 | Lau et al. | |
| 6,779,278 | B1 | * | 8/2004 | Spady et al. | 33/569 |
| 7,105,956 | B2 | * | 9/2006 | Botos et al. | 310/12 |
| 2002/0015140 | A1 | * | 2/2002 | Yoda | 355/53 |
| 2002/0117109 | A1 | * | 8/2002 | Hazelton et al. | 118/620 |
| 2004/0233412 | A1 | * | 11/2004 | Ono et al. | 355/72 |
| 2005/0236910 | A1 | * | 10/2005 | Botos et al. | 310/12 |

* cited by examiner

*Primary Examiner*—Darren Schuberg
*Assistant Examiner*—John K Kim
(74) *Attorney, Agent, or Firm*—The Webb Law Firm (57) ABSTRACT

A high precision z-theta stage having a horizontal translation axis (z-axis) and a rotary axis (theta-axis) parallel with the translation axis comprises parallel spaced apart linear translation stages, a carriage supported between the parallel translation stages, and a rotation stage carried by the carriage between the parallel translation stages. Each brushless linear motor is connected to the carriage to apply translation forces in a horizontal plane intersecting the vertical center of gravity.

12 Claims, 7 Drawing Sheets

WATER COOLED HIGH PRECISION Z-THETA STAGE

BACKGROUND OF THE INVENTION

This patent relates to an improved high precision z-theta stage. The stage has a horizontal translation axis (z-axis) and a rotary axis (theta-axis) parallel with the horizontal translation axis. Stages of this type are described in our co-pending U.S. application Ser. No. 10/830,979. The stage is especially designed for the manufacture of expandable stents for implantation in a human body or other cylindrical laser-machined components. The stents are manufactured from a tubular feedstock, such as stainless steel, nitanol, or plastic, and are provided with intricate circumferential patterns. Processes for machining the patterns out of the feedstock include laser machining in which a z-theta stage controlled by a CNC controller presents the feedstock to a laser beam for cutting away portions of the tubular feedstock. See U.S. Pat. No. 6,511,504 entitled "Expandable Stents and Method for Making Same" for a description of one stent manufacturing process. Due to the superior ability of the stage as described in our co-pending application to rapidly reposition without the need for setting delays, the throughput is so significantly increased that the ability of the rotation stage to dissipate heat limits further increase. It is an object according to this invention to overcome this limitation.

SUMMARY OF THE INVENTION

Briefly, a high precision z-theta stage has a horizontal translation axis (z-axis) and a rotary axis (theta-axis) parallel with the translation axis. The z-theta stage comprises a base plate having upper surfaces lying in a plane and parallel spaced apart linear translation stages each having parallel linear bearings with bearing surfaces mounted at a substantially equal distance from the planar surfaces of the base plate. Each linear translation stage has a brushless linear motor. A carriage is supported between the parallel translation stages by the linear bearings. A rotation stage is housed in the carriage between the parallel translation stages, the rotation stage comprises a brushless rotating motor having a shaft journaled with an axis parallel to the linear bearings. The carriage and rotation stage have a vertical and a horizontal center of gravity. Each brushless linear motor is connected to the carriage by applying translation forces in a horizontal plane intersecting the vertical center of gravity of the carriage. The improvement, according to this invention, comprises a cooling fluid labyrinth surrounding the armature case of the rotating motor.

A linear position feedback device comprising a resolver, a laser interferometer, or an encoder may be associated with one or both brushless linear motors. A rotary feedback device comprising a resolver or encoder may be associated with the brushless rotating motor.

The high precision z-theta stage may have a fluid-actuated, workpiece-holding chuck or collet attached to the rotor.

The rotor is preferably hollow to permit a cylindrical workpiece and/or a fluid cooling jacket to be advanced therethrough or positioned therein.

Most preferably, an auxiliary tooling platform is part of the base and is arranged to support brackets guiding, grasping, and feeding a workpiece along the axis of the rotor.

According to an alternate embodiment, the high precision translation stages support two identical carriages facing each other, each carrying an identical rotation stage.

According to another alternate embodiment, the precision z-theta stage has a carriage supporting two or more identical rotation stages.

Preferably, the horizontal center of gravity of the carriage and rotary stage is located halfway between each linear motor.

Preferably, each linear stage contains a linear motion guide, cross roller, or air bearing.

Preferably, each linear motor is connected to the carriage at multiple locations spaced in the direction of linear translation.

BRIEF DESCRIPTION OF THE DRAWINGS

Further features and other objects and advantages will become clear from the following detailed description made with reference to the drawings in which.

DESCRIPTION OF THE PREFERRED EMBODIMENTS

Figure 1:
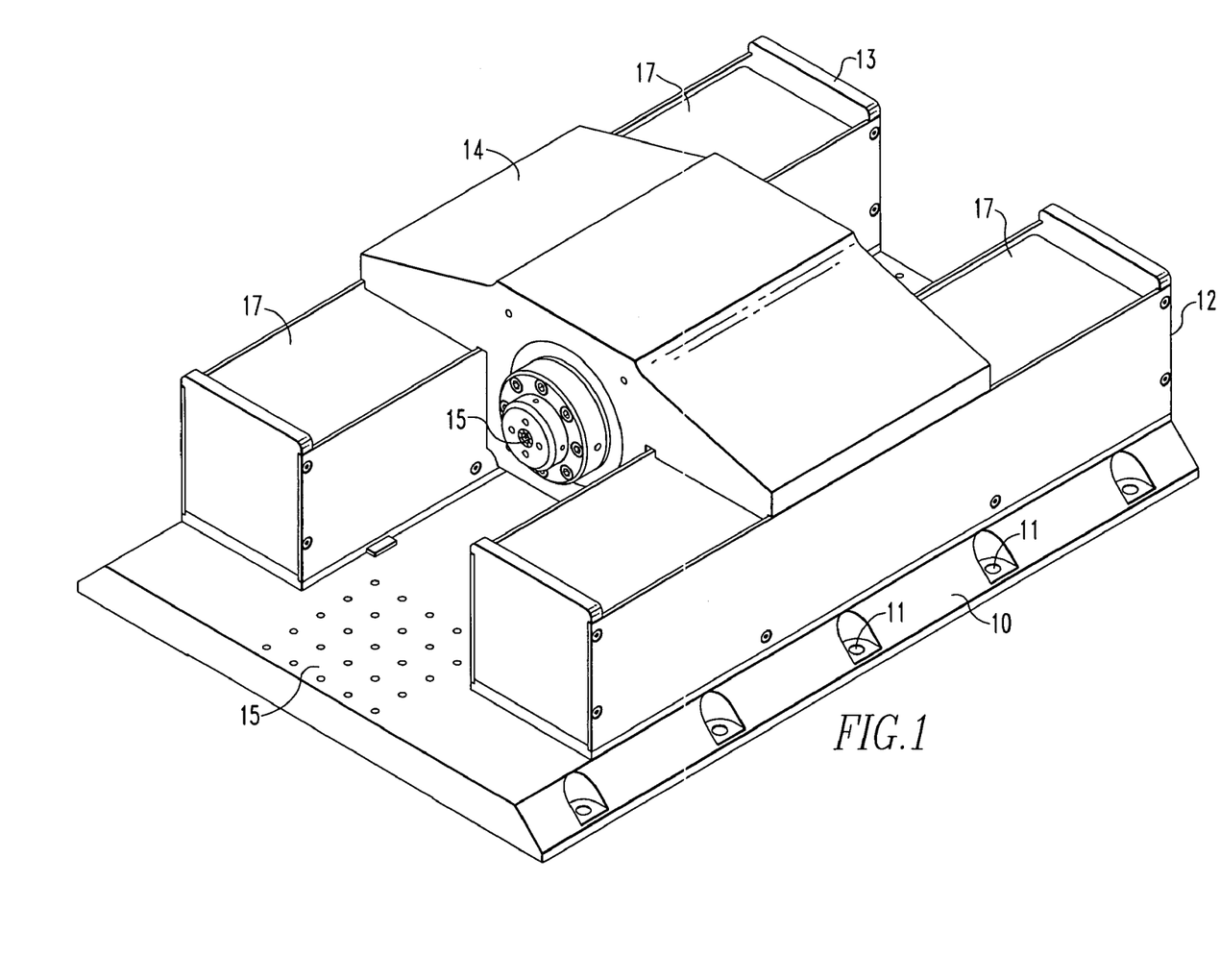
FIG. 1 is a perspective view of a z-theta stage according to this invention having a single rotary stage.

Referring to FIG. 1, there is shown a z-theta stage suitable for manufacture of precision parts, such as stents. The stage includes a base plate 10 which is provided with openings 11 to receive bolts for securing the stage to a foundation which is usually a large piece of granite, casting, or welded structure. The base plate 10 is fabricated from metal, steel, or aluminum, for example. Mounted to the base plate are two parallel linear motors 12 and 13. Mounted between the linear motors and carried by them is a carriage 14 which supports a rotary motor 15 having an axis parallel to the translation axes of the linear motors. Preferably, the z-axis is horizontal or substantially horizontal. The linear motors define the z-axis and the rotary motor the theta-axis of the z-theta stage. An essential feature of this invention is that the linear motors are connected to the carriage to apply translation forces to the carriage directed along the surface of a plane that includes the vertical center of gravity of the carriage or passes as close to the vertical center of gravity as mechanically possible. In this way, the angular displacement between the axis of rotation of the rotary motor and the z-axis plane during a period of rocking following a translation movement is substantially eliminated. Practically speaking, the plane along which the translation forces are applied passes within 1 mm of the vertical center of gravity of the carriage. The axis of rotation of the rotary motor may hang somewhat below the plane upon which translation forces are applied.

Figure 2:
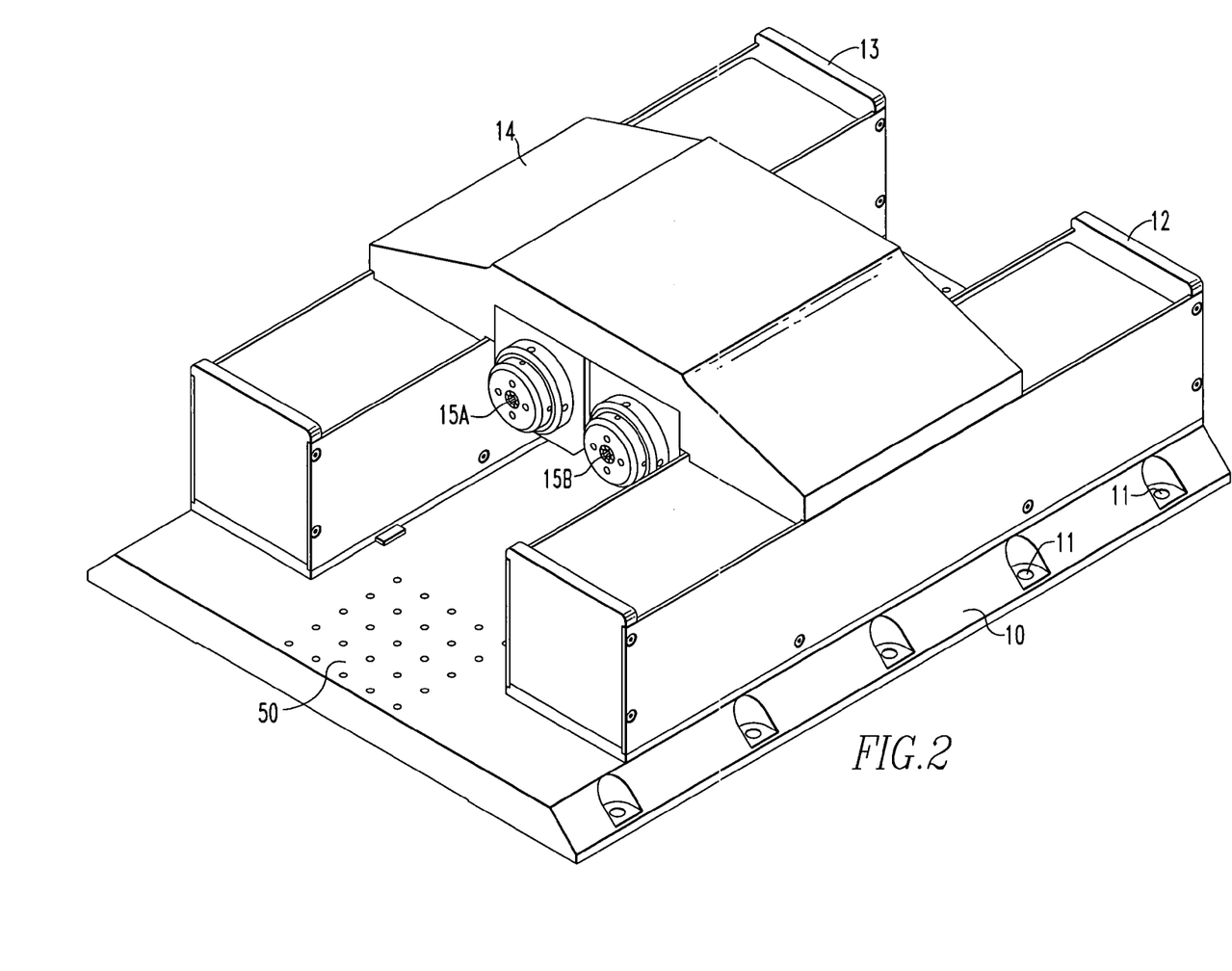
FIG. 2 is a perspective view of a z-theta stage according to this invention having a dual rotary stage.

FIG. 2 illustrates a variation of the z-theta stage shown in FIG. 1 in which dual theta stages (rotary motors 15A and 15B) are arranged side by side having parallel axes. It would be possible to process two workpieces simultaneously with this arrangement. In FIG. 2, identical elements are given identical numbers to those given for FIG. 1.

Figure 3:
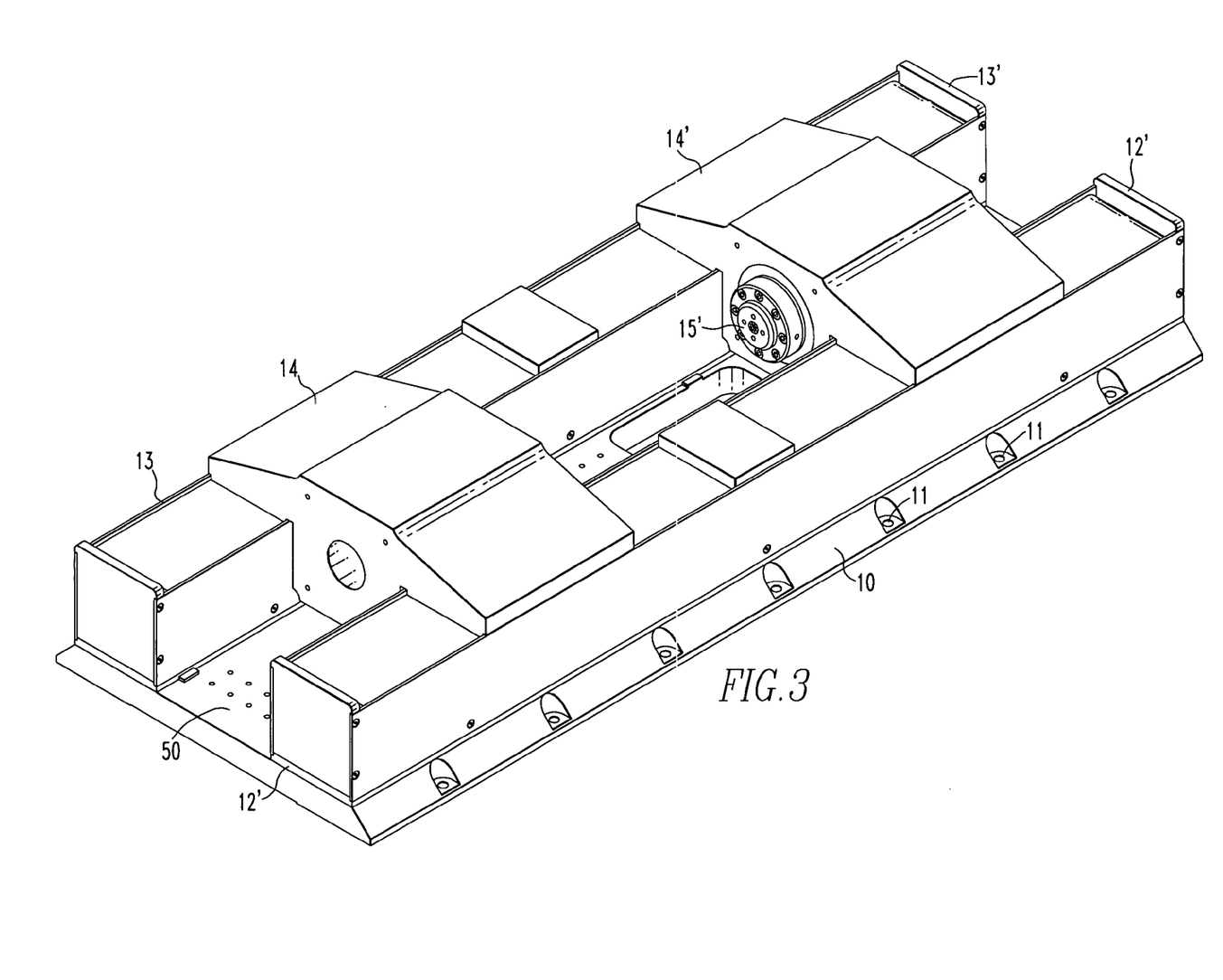
FIG. 3 is a perspective view of a z-theta stage according to this invention having two rotary stages mounted in line.

FIG. 3 illustrates another variation of the z-theta stage according to this invention in which two z-theta stages are aligned on the same base plate. In FIG. 3, identical elements are given identical numbers to those given for FIG. 1 and duplicate identical elements are given identical numbers with a prime. The advantage of this configuration is that the moving parts move the opposite direction on the stages. Thus, the forces generated during acceleration are cancelled, minimizing the forces transmitted to the structure, resulting in significantly reduced settling time.

The linear motors 12 and 13 are preferably permanent magnet linear motors, for example, direct drive brushless linear motors consisting of a noncontacting forcer coil 24 and a U-channel rare-earth magnet track 22. This design eliminates backlash, windup, wear, and maintenance associated with ball screws. Motors of this type are available from, among others, Aerotech, Inc of Pittsburgh, Pa.

The rotary motor 15 is preferably a rotary brushless rare-earth magnet servomotor. It forms the basis of a direct drive theta stage. Preferably, the rotating shaft has an axial bore and is provided with an air operated collet chuck. A motor of this type is available from Aerotech, Inc. of Pittsburgh, Pa.

Figure 4:
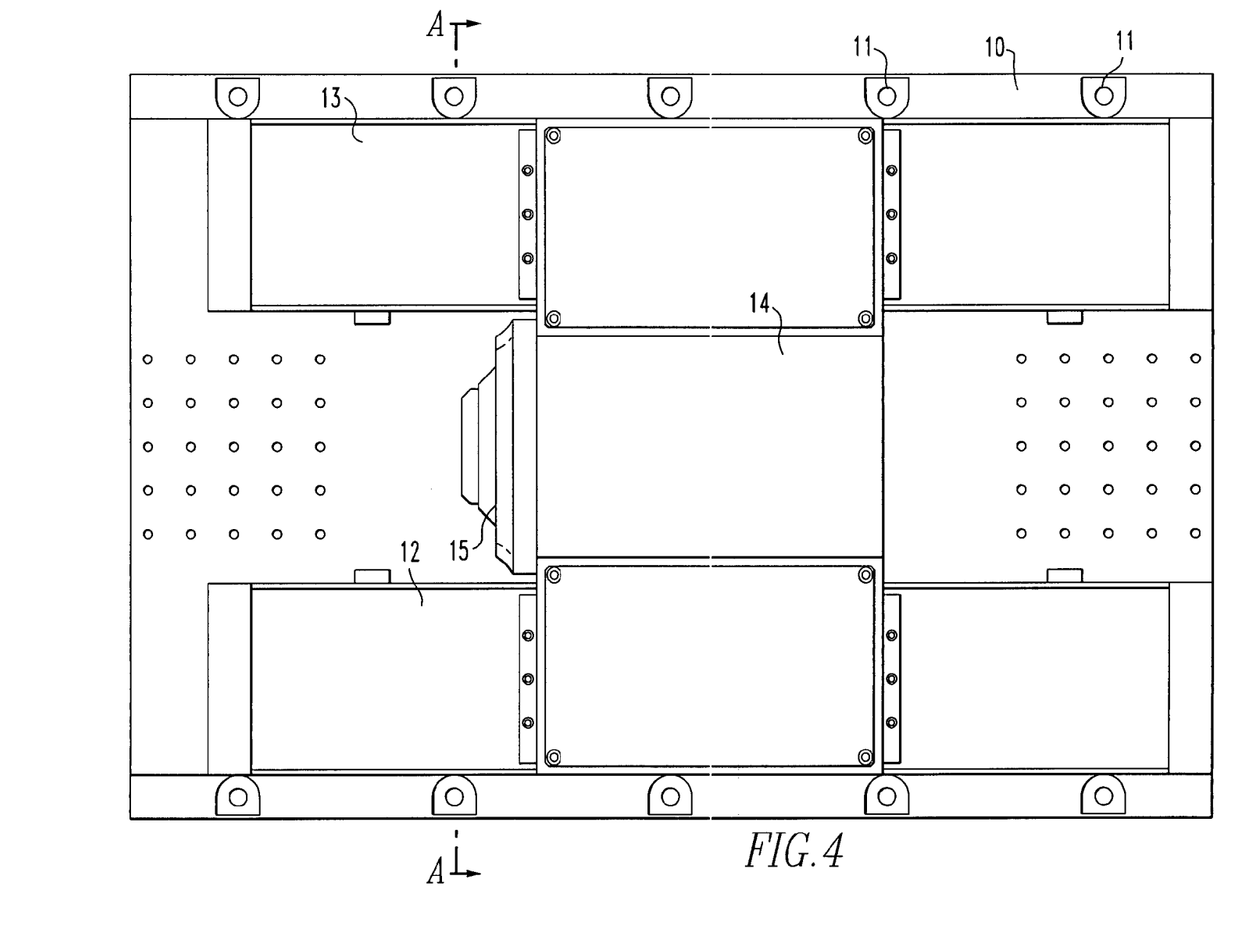
FIG. 4 is a plan view of the z-theta stage of FIG. 1.

Referring now to FIG. 4, the linear motors 12, 13 are shown spaced apart, parallel, and positioned on the base plate 10. Associated with the motors are linear motion guides or bearings which may have, for example, cross roller bearings or air bearings. The rotary motor 15 is spaced with an equal distance between itself and the linear motors and with a rotating axis parallel to the linear motors.

Figure 5:
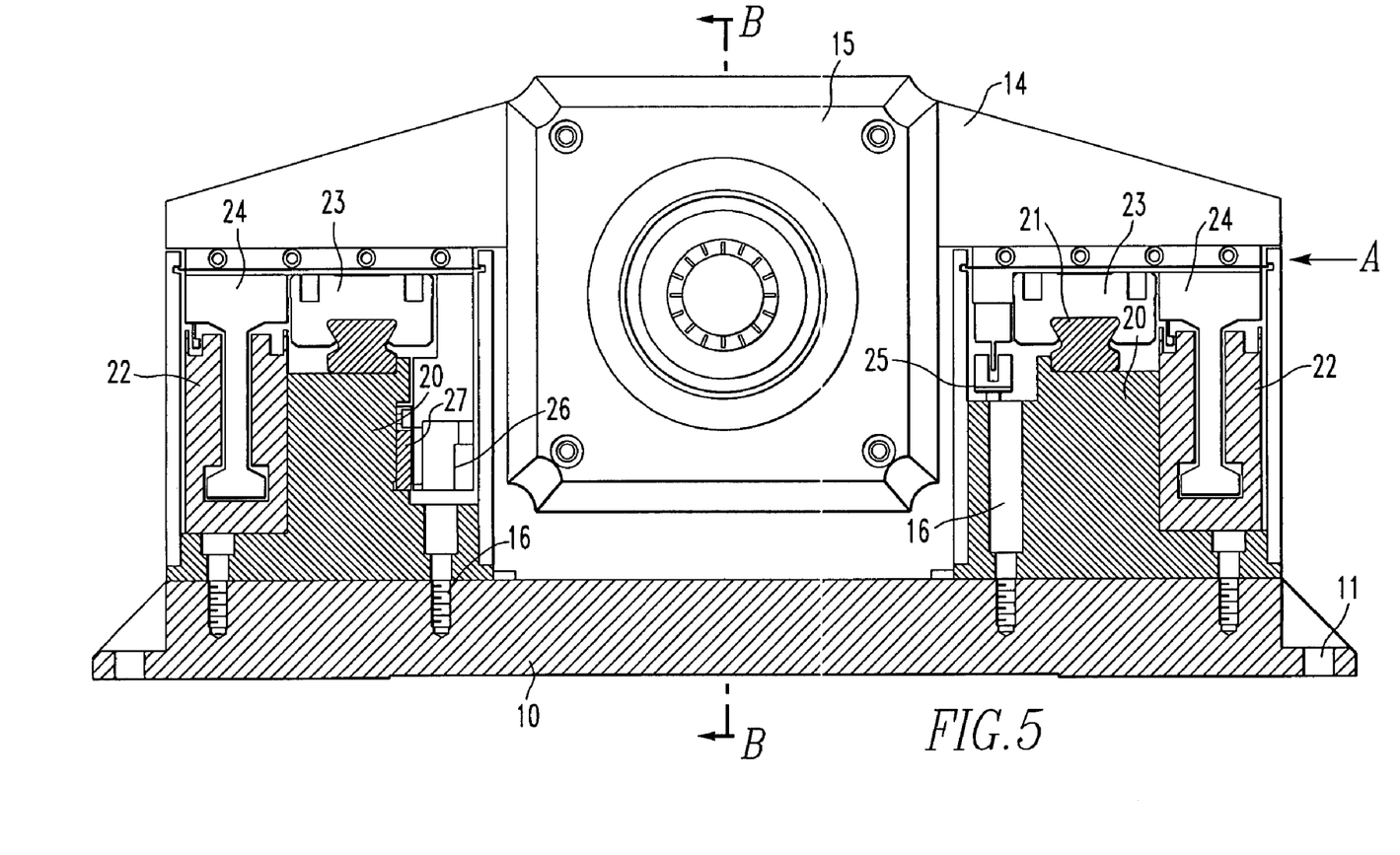
FIG. 5 is a section view along line A-A on FIG. 4 which is taken perpendicular to the theta-axis.
Figure 7:
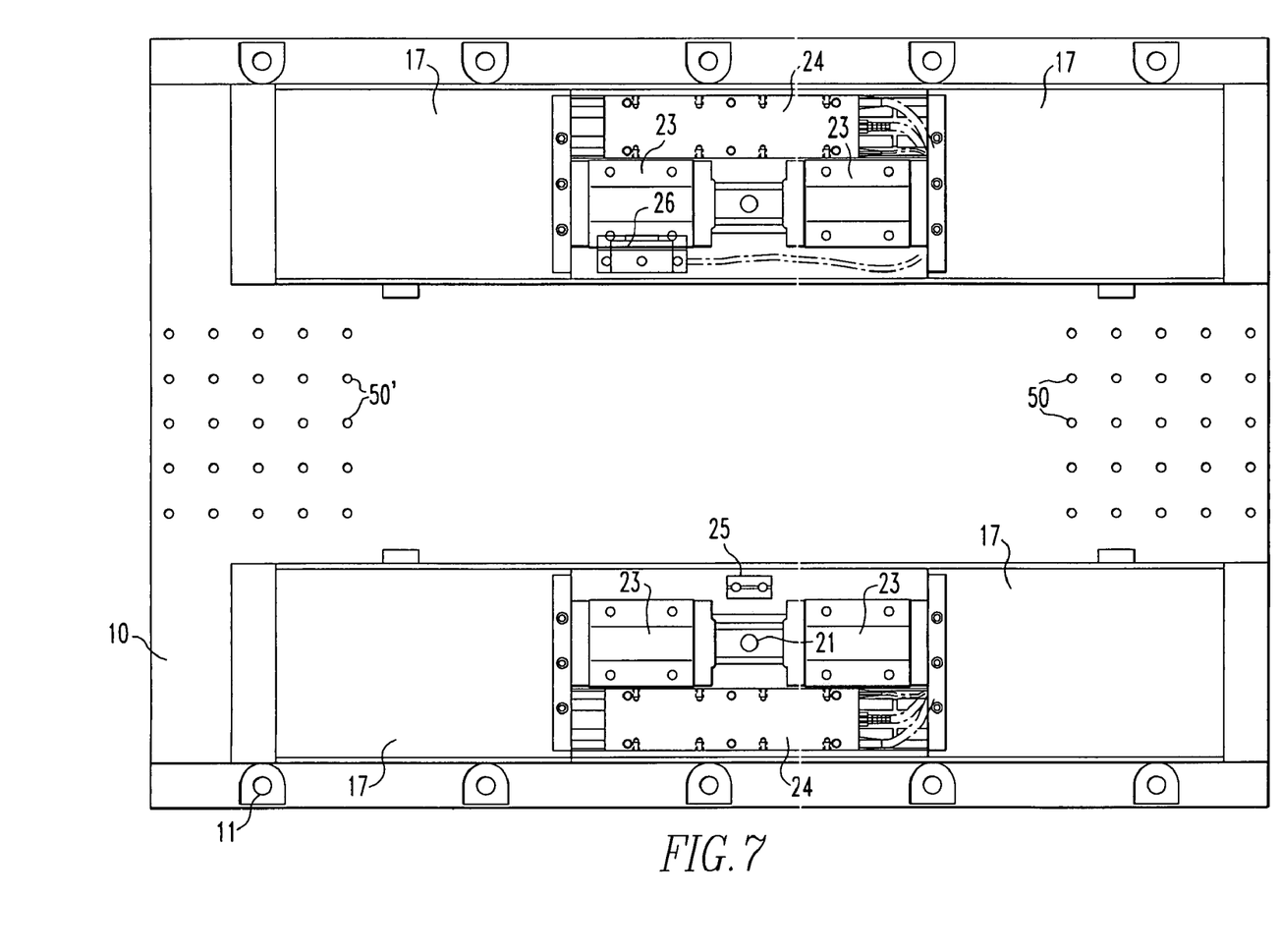
FIG. 7 is a plan view of the z-theta stage of FIG. 1 with the carriage removed.

Referring to FIG. 5, the linear motors are comprised of a linear spar 20 that is bolted the base plate 10 by bolts 16. The linear spar supports the track 21 of the linear bearing and the U-shaped magnet track 22. The magnet track 22 is a U-shaped channel fabricated from magnetic steel. It supports the rare-earth permanent magnets (not illustrated) arranged with alternating North and South poles facing inward at the forcer windings 24 along the length of the magnet track. The forcer windings are comprised of nonmagnetic materials so as not to be attracted by the magnet track 22. Bearing trucks 23 ride on the tracks 21 of the linear bearings and support the carriage 14. The forcer windings 24 are also secured to the carriage 14. As shown in FIGS. 5 and 7, the linear motor on the right side has a limit switch 25 associated therewith and the linear motor on the left side has an encoder read head 26 and encoder scale 27 associated therewith. As can be seen from FIG. 5, the linear motor applies translation forces to the carriage where the forcers are attached to the carriage (see arrow A in FIG. 5).

Attached to the carriage 14 and sliding over the linear motors 12, 13 is a flexible sliding cover 17. The cover 17 slides over rollers 18 (see FIG. 6) guided downward at each end of the linear motors.

Figure 6:
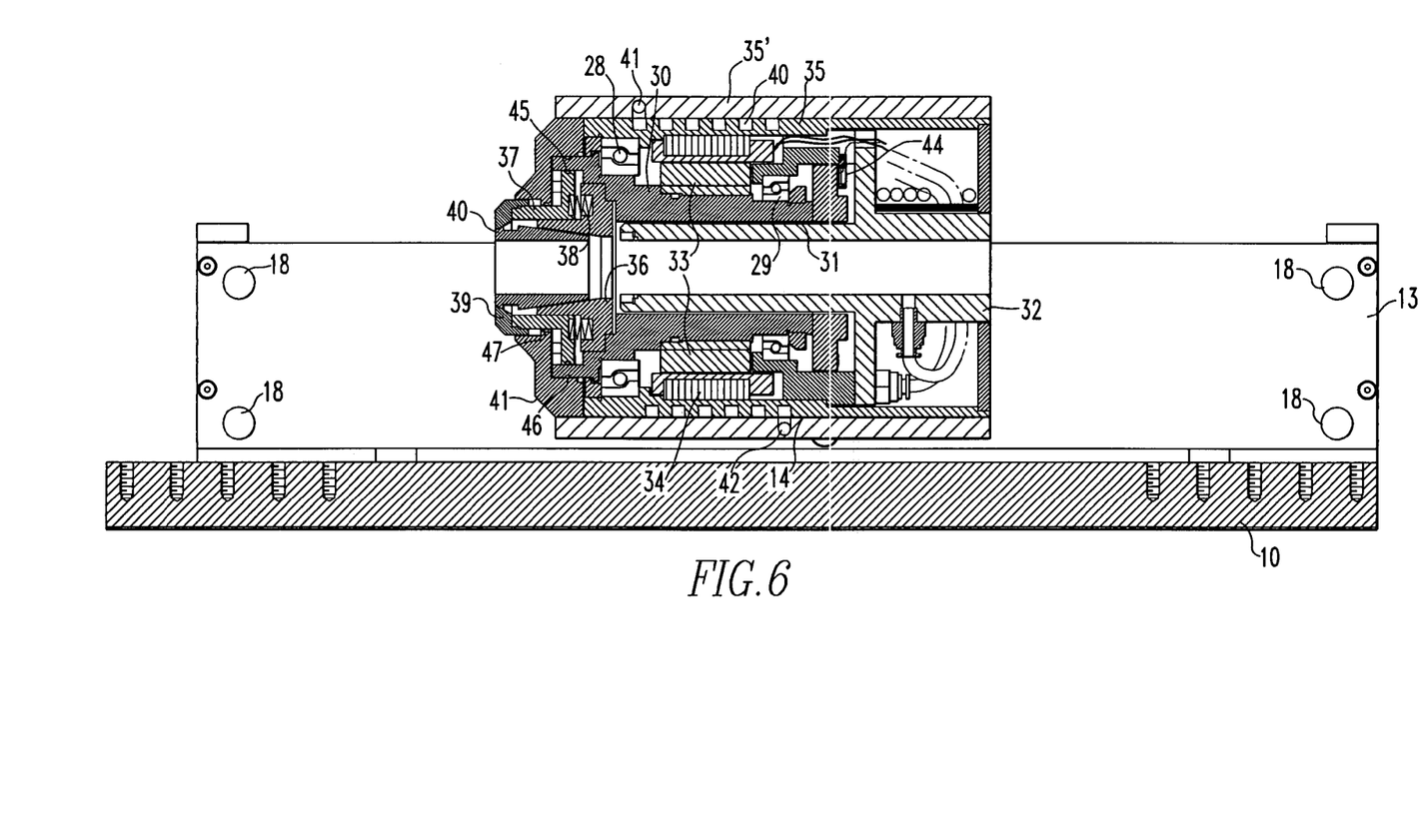
FIG. 6 is a section view along line B-B on FIG. 5 which is taken along the theta-axis.

Referring to FIG. 6, the rotary motor 15 carried by the carriage 14 will now be described. Bearings 28 and 29 support rotating shaft 30 from an armature case 35 that is integral with the carriage 14. Armature windings 34 are secured to the armature case 35 in a typical manner. The windings may be supported by a laminated magnetic core with slots for receiving the windings or the windings may not be supported by a core with slots (i.e., slotless). Permanent magnets 33 are secured to the outer cylindrical surface of the shaft 30 in a typical manner. A rotary encoder scale 43 is attached to the shaft. A rotary encoder readhead 44 is attached to armature casing 35.

The armature casing is provided with a sealable labyrinth through which cooling fluid may be forced. As shown in FIG. 6, the armature casing has spiral or interconnected circumferential grooves cut into the armature casing and a cylindrical jacket enclosing the grooves 40. A first input/output port 41 is provided in communication with the labyrinth at one location and a second input/output port in communication with the labyrinth is provided at a spaced location. Each port is provided with a fitting enabling the connection of flexible supply and drain tubes. It is preferable if the supply port is near the lower side of the armature casing and the drain is near the top side. In this way, the entire labyrinth will be constantly filled with fluid, for example, water. Thus, the center of gravity of the carriage will remain constant.

According to one particularly advantageous embodiment, the armature winding is slotless and the shaft is made of aluminum or another lightweight metal. While the torque/inertia ratio for this embodiment is low, the absence of cogging due to the slotless winding results in a superb theta stage for manufacture of stents.

The shaft has a bore 31 extending end to end. In a particularly advantageous embodiment, nested within the bore 31 is a water jacket assembly 32 for cooling the shaft and a workpiece held in the shaft.

The bore 31 of the shaft 30 stepwise widens at one end to form two cylindrical seats, one having a larger diameter than the other. A tapered collet chuck 36 is fixed in the cylindrical seat of lesser diameter. A piston 37 rides within the seat of larger diameter and is telescoped over the tapered collet chuck 36. The piston 37 is biased by spring 38 towards the tapered collet chuck. Threaded to the piston is an annular threaded retaining cap 39 that has a tapered inner rim. A collet 40 is positioned to slide within the tapered collet chuck 36 and is held in place by the tapered inner rim of the retaining cap 39. According to one preferred embodiment, the collet 40 is of the ER-16 series available in multiple sizes from 0.05 mm to 10 mm. An annular manifold 41 is secured to the armature case 35. A piston chamber is formed between the manifold 41, the piston 37, and the larger diameter seat. Seals 45, 46, 47 are provided between the piston and the large diameter seat, between the shaft and the manifold, and between the manifold and the piston, respectively. A passage (not shown) is in communication with the piston chamber and a fitting is provided on the outside of the manifold 41 for supplying pressurized air to the piston chamber to force the piston over the collet to tighten the collet onto a workpiece (not shown). In this embodiment, the air pressure engages the collet with the workpiece; however, the piston can be arranged such that air pressure would release the collet.

The base plate 10 has at least one auxiliary tooling platform 50, 50' (see FIG. 7) arranged to support brackets guiding, grasping, and feeding a workpiece along the axis of the rotor.

The linear motors and rotary motor have associated position feedback means. In the specific embodiment described herein, position feedback is supplied from encoders. However, other position feedback means include resolvers and laser interferometers.

Incremental encoders are commonly used measurement transducers. Optical incremental encoders pass light from a lamp or light-emitting diode at a grating attached to the axis to be measured. The grating normally has two tracks offset 90 degrees apart with respect to each other (in quadrature). A single marker on a third track serves as a home marker (in the case of a rotary encoder, a one-per-revolution marker). The light reflected from the grating continues through a reticule or mask which, together with the grating, acts as a shutter. The shuttered light falling on a detector results in the generation of electrical signals. These signals are amplified and output as two amplified sinusoidal or square waves in quadrature and are output on two separate channels as signals SIN and COS. With simple incremental encoders, the position is measured by counting the zero crossings (sinusoidal) or edges (square waves) of both channels. Where greater precision is required, the amplified sinusoidal signals (SIN and COS) are sent to an encoder multiplier where the intermediate positions are resolved at spaced time intervals.

An encoder multiplier uses the SIN and COS signals to resolve many positions within one grating period (scribe lines). The multiplier, for example, is able to produce up to 65,000 transitions within one grating period as opposed to the four by a simple incremental encoder. See, for example, U.S. Pat. No. 6,356,219 entitled "Calibrated Encoder Multiplier". Feedback from the incremental encoders can be used to control the currents applied to each phase of the windings to precisely position the stages.

Having thus defined our invention in the detail and particularity required by the Patent Laws, what is desired protected by Letters Patent is set forth in the following claims.

The invention claimed is:

1. A high precision z-theta stage having a horizontal translation axis (z-axis) and a rotary axis (theta-axis) parallel with the translation axis comprising:
   a base plate having upper surfaces lying in a plane;
   parallel spaced apart linear translation stages each having parallel linear bearings with bearing surfaces mounted at a substantially equal distance from the planar surfaces of the base plate, each linear translation stage having a brushless linear motor;
   a carriage supported between the parallel translation stages by the linear bearings; and
   a rotation stage carried by the carriage between the parallel translation stages, said rotation stage comprising a brushless rotary motor having a shaft journaled with an axis parallel to the linear bearings, the carriage and rotation stage having a vertical and a horizontal center of gravity,
   each brushless linear motor being connected to the carriage to apply translation forces in a horizontal plane intersecting said vertical center of gravity, said brushless rotary motor comprising a permanent magnet rotor and a surrounding armature casing supporting an armature winding on the inner diameter thereof, said armature casing having a cooling fluid labyrinth formed in the casing with an inlet and outlet port in communication through the labyrinth.

2. The high precision z-theta stage according to claim 1, wherein a linear position feedback device means is associated with one brushless linear motor.

3. The high precision z-theta stage according to claim 1, wherein a linear position feedback means is associated with each brushless linear motor.

4. The high precision z-theta stage according to any one of claims 1 to 3, wherein a rotary feedback means is associated with the brushless rotary motor.

5. The high precision z-theta stage according to any one of claims 1 to 3 having a fluid-actuated, workpiece-holding chuck or collet attached to the shaft of the rotary motor.

6. The high precision z-theta stage according to any one of claims 1 to 3, wherein the shaft of the rotary motor is hollow to permit a cylindrical workpiece and/or a fluid cooling jacket to be positioned therein.

7. The high precision z-theta stage according to any one of claims 1 to 3 further comprising an auxiliary tooling platform for holding brackets for guiding and feeding a workpiece along the axis of the shaft of the rotary motor and being axiaily spaced therefrom.

8. The high precision z-theta stage according to claim 1, wherein the parailel translation stages support two identical carriages facing each other, each carrying an identical rotation stage.

9. The high precision z-theta stage according to claim 1, wherein the carriage supports at least two identical rotation stages.

10. The high precision z-theta stage according claim 1 in which the horizontal center a gravity of the carriage and rotary stage is halfway between each linear motor.

11. The high precision z-theta stage according to claim 1 in which each linear stage contains a linear motion guide, cross roller bearing or air bearing.

12. The high precision Z-theta stage according to claim 1 in which each linear motor is connected to the carriage at multiple locations spaced in the direction of linear translation.

* * * * *

UNITED STATES PATENT AND TRADEMARK OFFICE
CERTIFICATE OF CORRECTION

PATENT NO.       : 7,420,298 B2
APPLICATION NO.  : 11/169514
DATED            : September 2, 2008
INVENTOR(S)      : Botos et al.

Page 1 of 1

It is certified that error appears in the above-identified patent and that said Letters Patent is hereby corrected as shown below:

Column 6, Line 24, Claim 7, "axiaily spaced" should read -- axially spaced --

Column 6, Line 26, Claim 8, "parailel translation" should read -- parallel translation --

Column 6, Line 33, Claim 10, "center a gravity" should read -- center of gravity --

Signed and Sealed this

Thirteenth Day of January, 2009

JON W. DUDAS
*Director of the United States Patent and Trademark Office*